US00PP09299P

United States Patent [19]

Evison

[11] Patent Number: Plant 9,299

[45] Date of Patent: Sep. 26, 1995

[54] CLEMATIS NAMES 'EVIFOUR'

[75] Inventor: Raymond J. Evison, Guernsey, Great Britain

[73] Assignee: The Guernsey Clematis Nursery Limited, United Kingdom

[21] Appl. No.: 331,039

[22] Filed: Oct. 28, 1994

[51] Int. Cl.[6] ..... A01H 5/00

[52] U.S. Cl. ..... Plt./54.1

[58] Field of Search ..... Plt./54.1, 68.1

*Primary Examiner*—James R. Feyrer
*Attorney, Agent, or Firm*—Christie, Parker & Hale

[57] ABSTRACT

A new variety of Clematis having repeat flowering habit and suitable for growing in a container.

1 Drawing Sheet

BACKGROUND OF THE INVENTION

This invention relates to a new and distinct variety of Clematis. The varietal denomination of the new variety is 'Evifour'. It was discovered as a seedling in a controlled planting of cultivated plants in St. Sampsons Parish, Guernsey, Channel Islands, Great Britain, and its parents are not known.

SUMMARY OF THE INVENTION

Among the features which distinguish the new variety from other presently available and known commercial clematis cultivars are the following combination of characteristics: recurrent blooming habit and free flowering characteristic, attractive violet flowers and compact habit which makes it ideal for growing in containers. 'Evifour' is asexually propagated by vegetative cuttings and asexual reproduction of new variety as performed by vegetative cuttings in Guernsey, Channel Islands, Great Britain, shows that the foregoing and other distinguishing characteristics come true to form and are established and transmitted through succeeding propagations.

BRIEF DESCRIPTION OF THE ILLUSTRATION

The accompanying photographic illustration shows the foliage, flower buds and flowers of the new variety, with different flowers shown in various stages of maturity. The flower poise, contrasting colors, petal count and petal characteristics are depicted. The domed boss of stamens is shown forming the attractive center of the flowers and the coloration and character of the foliage can be seen behind the flowers. The coloration shown in the photograph is as nearly correct as is possible in color illustrations of this character. Throughout the specification color values are based upon the *Royal Horticultural Colour Chart,* Royal Horticultural Society of London, England, except where common terms of color definition are employed.

DESCRIPTION OF THE NEW VARIETY

The following description is of clematis plants of the new cultivar grown under glass at Guernsey, Channel Islands, Great Britain throughout the flowering period. Phenotypic expression may vary with environmental, cultural and climatic conditions, as well as differences in conditions of light and soil.

Plant

A. Form: Upright climbing or spreading.
B. Growth: Medium growth, compact habit.
*Height attained.*—About 2 meters.
C. Foliage: Deciduous, compound — tri-folate, sometimes simple.
1. *Size.*—Medium.
2. *Quantity.*—Average.
3. *Color.*—New foliage: Upper side — light green, occasional red edging. Underside — light green. Old foliage: Upper side — green, near 137A. Underside — light green, near 137C.
4. *Shape.*—Lower leaves sometimes simple; normally 3 ovate leafles in pinnate form.
5. *Texture.*—Upper side — glabrous, veined. Underside — ribbed.
6. *Edge.*—Leaf edge occasionally shows red/purple.
7. *Serration.*—None.
8. *Petiole color.*—Top surface — green/red. Underside — green/red.
9. *Stipules.*—None.
10. *Internodes.*—Cylindrical. About 12 cm to about 17 cm.
11. *Resistance to disease.*—Subject to any disease that normally affects clematis but less prone to mildew than some Clematis.
D. Wood:
1. *New shoots.*—Color — light green, turning deep red/purple. Bark — smooth — light white hairs.
2. *Old wood.*—Color — light brown. Bark — rough.
E. Hardiness: Zone 4–9.

Flower

A. Blooming habit: Recurrent.
B. Bud:
1. *Size.*—About 4 cm to about 5 cm.
2. *Form.*—Elliptic to ovate.
3. *Color.*—Green/grey turning slightly red with age, hairy.
C. Sepals: None — tepals only.
D. Penduncle:
1. *Length.*—About 5 cm to about 8 cm.
2. *Aspect.*—Vertical.
3. *Strength.*—Erect.
4. *Color.*—Green, turning red/purple with age, near 59A.
E. Bloom:
1. *Size.*—About 12 cm to about 16 cm.
2. *Borne.*—Singly.

3. *Form.*—Tepals opening to become flat, tepal tip becoming recurving when mature.
4. *Petalage.*—6 tepals.
5. *Color.*—Outer tepals: Top surface — violet, near 83B. Undersurface — violet, near 83C. Base of tepals: Pale violet. General tonality from a distance: Velvet.
6. *Color change.*—As bloom ages, colors lighten, though center of tepal often remains dark, occasionally giving impression of darker central bar. General tonality at a distance: Pale velvet.

F. Tepals:
1. *Texture.*—Medium/thick.
2. *Appearance.*—Top surface — velvet. Under surface — matt.
3. *Form.*—Obovate.
4. *Arrangement.*—Regularly arranged.
5. *Petaloids in center.*—None.
6. *Persistence.*—Tepals are persistent.
7. *Fragrance, if any.*—None.
8. *Lasting quality on plant and after cutting.*—About two weeks on plants, lasting only a few days as a cut flower.

Reproductive organs

A. Stamens, filaments and anthers:
1. *Arrangement.*—Regularly arranged.
2. *Color.*—Stamens: White base, red-purple tip. Filaments: White, apex pink-red. Anthers: Dark red/purple, near 71A.

B. Pollen:
*Color.*—Off white.

C. Styles: Bunched, even, average length.

D. Stigmas:
*Color.*—Pink-white.

E. Hips:
*Shape.*—None.

I claim:

1. A new and distinct variety of Clematis substantially as described and illustrated herein.

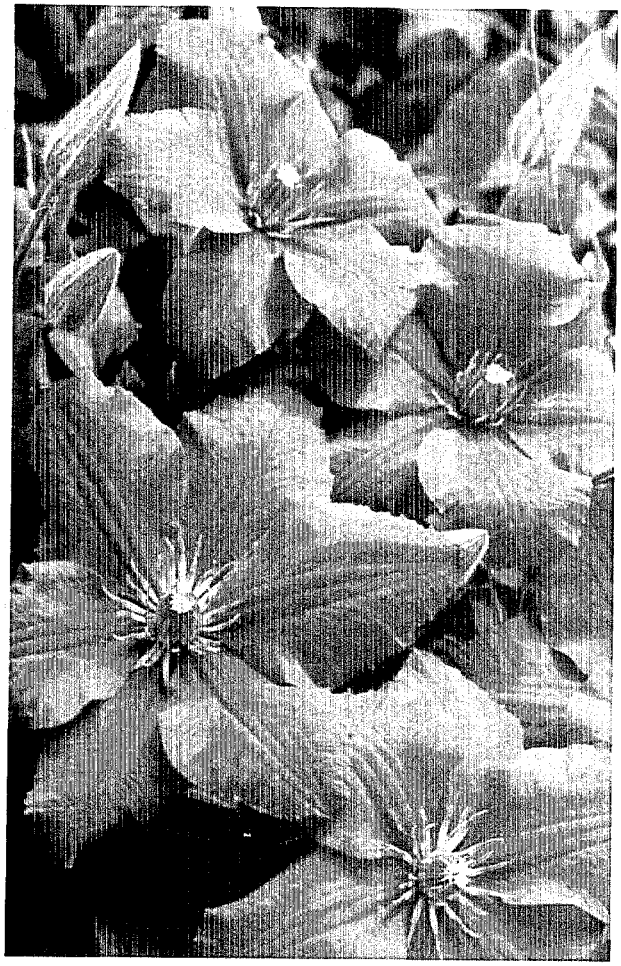

* * * * *